(12) United States Patent
Gemmiti et al.

(10) Patent No.: US 11,666,836 B2
(45) Date of Patent: Jun. 6, 2023

(54) EXTRACTION OF CANNABINOIDS FROM CANNABIS

(71) Applicants: CannTrust Inc., Vaughan (CA); Single Dose Solutions Inc., Toronto (CA)

(72) Inventors: Claudio Gemmiti, Toronto (CA); Ilana Deborah Platt, Toronto (CA)

(73) Assignee: CannTrust Inc. and Single Dose Solutions Inc., Vaughan and Toronto (CA)

(*) Notice: Subject to any disclaimer, the term of this patent is extended or adjusted under 35 U.S.C. 154(b) by 363 days.

(21) Appl. No.: 16/963,884

(22) PCT Filed: Feb. 6, 2019

(86) PCT No.: PCT/CA2019/050157
§ 371 (c)(1),
(2) Date: Jul. 22, 2020

(87) PCT Pub. No.: WO2019/153083
PCT Pub. Date: Aug. 15, 2019

(65) Prior Publication Data
US 2020/0346135 A1    Nov. 5, 2020

Related U.S. Application Data

(60) Provisional application No. 62/629,363, filed on Feb. 12, 2018.

(51) Int. Cl.
*B01D 11/02*    (2006.01)
*C07D 311/80*    (2006.01)

(52) U.S. Cl.
CPC ........ *B01D 11/0288* (2013.01); *B01D 11/028* (2013.01); *B01D 11/0292* (2013.01); *C07D 311/80* (2013.01)

(58) Field of Classification Search
None
See application file for complete search history.

(56) References Cited

U.S. PATENT DOCUMENTS 9,730,911 B2    8/2017    Verzura et al.

OTHER PUBLICATIONS

Handa et al., Extraction Technologies for Medicinal and Aromatic Plants, International Centre for Science and High Technology, (Year: 2008).*
A&A Pharmachem, MCT—Oil and Oil Powder What's the Difference (Year: 2019).*
PCT, International Search Report and Written Opinion of the International Searching Authority relating to application No. PCT/CA2019/050157 dated Apr. 24, 2019.

* cited by examiner

*Primary Examiner* — Zinna Northington Davis
(74) *Attorney, Agent, or Firm* — Rowand LLP

(57) ABSTRACT

Methods and processes for efficiently extracting cannabinoids from cannabis are described together with cannabis extracts obtained using such methods. A method may include: preparing a premixture by mixing dried cannabis with an extraction agent; incubating the premixture; and after incubating the premixture, adding a liquid to the premixture to create a liquid mixture and filtering the cannabis from the mixture.

11 Claims, 1 Drawing Sheet

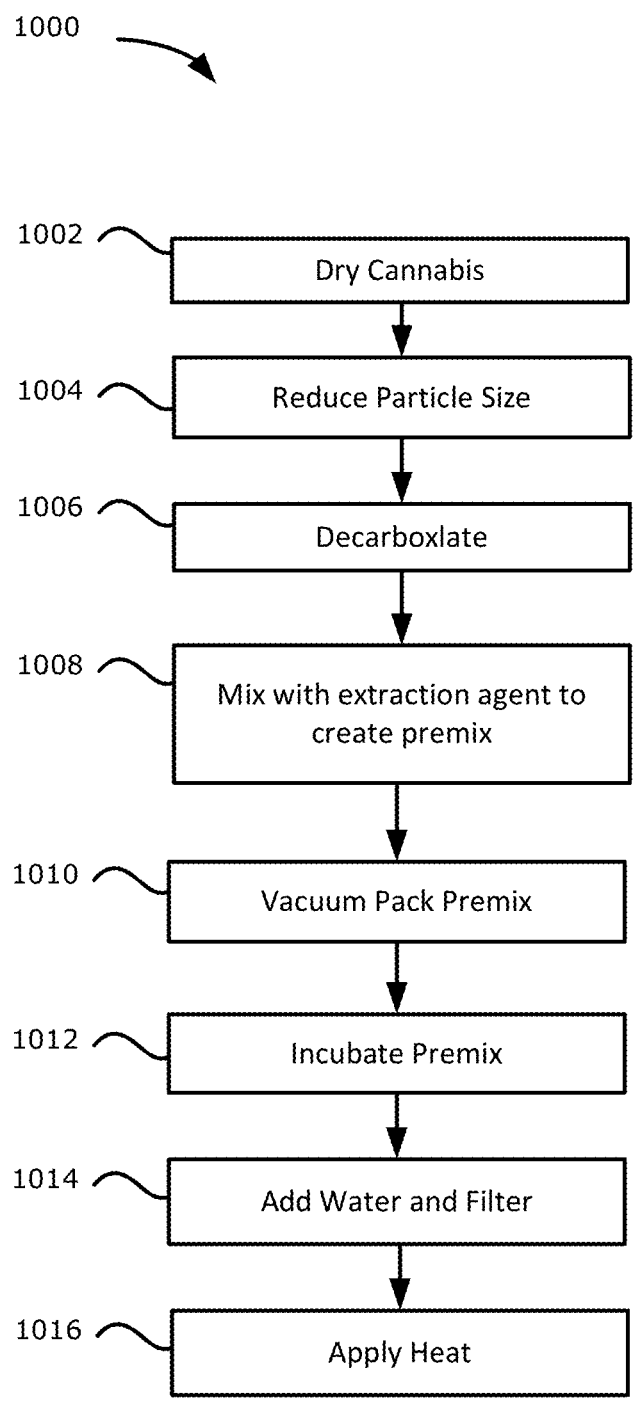

EXTRACTION OF CANNABINOIDS FROM CANNABIS

TECHNICAL FIELD

The present application relates to cannabis and, more particularly, to methods for extracting cannabinoids from cannabis and to cannabis extracts obtained using such methods.

BACKGROUND

Cannabis, which is commonly known as marijuana, is often used as a medicine for the treatment of a variety of conditions. Cannabis contains numerous cannabinoids, such as delta-9-tetrahydrocannabinolic Acid (THCA). Acidic cannabinoids, such as THCA and cannabidiolic acid (CBDA) may be converted to more active cannabinoids (which may also be referred to as neutral cannabinoids), through a process known as decarboxylation. For example, THCA is converted to delta-9-tetrahydrocannabinol (THC) through decarboxylation.

Decarboxylation is typically performed by smoking cannabis. The heat generated during smoking decarboxylates the acidic cannabinoids, such as THCA, into the neutral form, such as THC.

The use of smoking as a means for delivering the active ingredients in cannabis to a patient has a number of problems. For example, ensuring a proper dosage for medical marijuana users is difficult with smoking since each patient has different smoking tendencies which will affect the dose. More particularly, medical marijuana is often prescribed as a dose per day by weight for a patient. An example of a medical marijuana prescription may be 0.5 g of marijuana taken two times per day for a period of 30 days. Different users may, however, inhale a different amount of the active ingredients when smoking. For example, the actual dose for a patient (i.e. the amount actually consumed) will depend on variables such as the elapsed time between inhales, the amount of time that the patient holds the smoke in, the tightness of the cannabis cigarette, the moisture content of the cigarette (which may affect the burn rate between breaths) and other variables.

Also, some patients may be reluctant to smoke marijuana because of a stigma associated with smoking marijuana, perceived health concerns associated with smoking, or their inability to smoke effectively due to other medical conditions.

Vaporization is another common method of consuming cannabis. Vaporization also suffers from inconsistent dosing since variables such as temperature, inhalation duration and strength of inhalation will affect dosage.

Alternative methods of delivering cannabinoids from medical marijuana often involve obtaining cannabis extracts. For example, cannabis oils may be obtained from cannabis plants using a variety of techniques. By way of example, the cannabis may be immersed in a solvent to extract cannabinoids from the cannabis plant into the cannabinoid solvent. Solvent-based extraction can, however, yield byproducts that are environmentally harmful and that require special disposal (e.g., special waste removal fees may apply). Further, performing solvent-based extraction techniques often requires specialized equipment such as fume hoods, etc. Additionally, the solvents that are used in solvent-based extraction can be relatively expensive. There is also a concern among at least some cannabis users that cannabis extracts obtained using solvent-based extraction may include solvent residuals that may be harmful to such users.

Super-critical carbon dioxide ("CO2") extraction techniques are sometimes used as an alternative to solvent-based extraction techniques. More specifically, CO2 may be compressed at high pressures to become a supercritical or subcritical fluid which can then be used to strip the cannabinoids out of the cannabis plant. While such techniques have some benefits over solvent-based extraction, super-critical CO2 extraction also relies on specialized equipment which is very expensive.

Addition of these cannabinoid extracts may also be more difficult in food and/or beverage applications where little or no fat is present, thus requiring inclusion of a solubilizing agent in order to prepare an acceptable final food or beverage.

Thus, there is a need for alternative methods of delivering medical marijuana and alternative methods of extracting cannabinoids from cannabis.

BRIEF DESCRIPTION OF THE DRAWINGS

Reference will now be made, by way of example, to the accompanying drawings which show embodiments of the present application, and in which:

FIG. 1 is a flowchart of a method for extracting cannabinoids.

Like reference numerals are used in the drawings to denote like elements and features.

DETAILED DESCRIPTION OF EXAMPLE EMBODIMENTS

As will be described in greater detail below, methods and processes for efficiently extracting cannabinoids from cannabis are described together with cannabis extracts obtained using such methods.

In an aspect, a method of extracting cannabinoids from cannabis is described. The method may include: preparing a premixture by mixing dried cannabis with an extraction agent; incubating the premixture; and after incubating the premixture, adding a liquid to the premixture to create a liquid mixture and filtering the cannabis from the mixture. The liquid may be water.

The method may include, prior to mixing, pulverizing the cannabis to reduce a particle size of the cannabis.

The extraction agent used in the method may be a medium chain triglycerides (MCT) powder. The MCT powder may have a fat content that is greater than 65%, a protein level that is greater than 25% and a carbohydrate level of less than one percent.

The method may include heating the liquid mixture to evaporate the liquid and produce a cannabis extract. The cannabis extract may have a moisture content of one percent or less. Heating the liquid mixture to evaporate the liquid may include heating the liquid mixture at a temperature sufficient to decarboxylate.

Incubating the premixture may include storing the premixture for between two and fifteen days.

The method may include, prior to incubating, vacuum sealing the premixture.

The method may include, after filtering the cannabis, further filtering the liquid mixture to clarify the liquid mixture.

The method may include, prior to preparing the premixture, decarboxylating the cannabis.

In an aspect, the present application describes a cannabis extract produced according to a method described herein.

In the present application, the term "and/or" is intended to cover all possible combinations and sub-combinations of the listed elements, including any one of the listed elements alone, any sub-combination, or all of the elements, and without necessarily excluding additional elements.

The cannabis extracts, which may be powdered cannabis extracts, may be used in various ways including, for example, through inclusion in food products or inclusion in a tincture.

Referring now to FIG. 1, a method 1000 of extracting cannabinoids and other plant molecules from cannabis is illustrated. The method 1000 may, in some embodiments, be used to produce a cannabis extract, such as a powdered cannabis extract.

The method includes, at step 1002, drying cannabis. The cannabis that is dried at step 1002 may be of any strain including pure or hybrid varieties such as Cannabis sativa or Cannabis indica. The cannabis may be harvested before performance of the method 1000. The cannabis that is used in the method 1000 may include any of the bud, leaves, or fines portions of a cannabis plant, or a combination thereof. In at least some embodiments, the whole flower may be used in the steps described below to produce a whole flower extract.

During operation 1002, the cannabis is dried in order to reduce the moisture content of the cannabis. While some decarboxylation may occur in this stage, the intention of this stage is not to decarboxylate the cannabis but rather to dry the cannabis. The cannabis is, in some embodiments, dried in an oven. For example, in some embodiments, the cannabis may be dried in an oven at a temperature of 100 to 105 degrees Celsius for 10 to 20 minutes. In one embodiment, the cannabis is dried at 105 degrees Celsius for 15 minutes. The cannabis may be dried to have a defined moisture content. The defined moisture content may be less than ten percent moisture, for example.

The oven used in the drying may be a continuous process oven, such as a conveyor oven. A conveyor oven is an oven that is equipped with a conveyor which slowly moves the cannabis through a heating chamber at a predetermined speed until it reaches a position where it is expelled from the heating chamber. For example, cannabis may be added to the conveyor at an upstream end of the conveyor, which may be located outside the heating chamber. The cannabis is then drawn into the heating chamber due to movement of the conveyor and is slowly moved across the length of the heating chamber, where it eventually expelled from the heating chamber at a downstream end of the conveyor.

At step 1004, the cannabis may be processed to reduce the particle size of the cannabis. For example, the cannabis may be processed to have a desired average or maximum particle size. Accordingly, the cannabis may, at operation 1004, be pulverized, or otherwise broken apart into small particles. The pulverizing may be performed by impacting, beating, crushing, rolling, grinding or otherwise applying a force to the cannabis to break it apart. The pulverizing may be performed using a pulverizing machine. That is, the cannabis is inserted into the pulverizing machine and the pulverizing machine then impacts the cannabis to break it apart. For example, the pulverizing machine may be of a type commonly used in the food or drug industries.

In some embodiments, prior to the pulverizing, the cannabis is freeze dried in order to facilitate pulverization. The freeze drying may be performed by applying liquid nitrogen (or other freezing liquid or gas) to the cannabis. The freeze dried cannabis is then inserted into the pulverizing machine and the pulverizing performed. The freeze drying of the cannabis may be useful to ensure the pulverized cannabis has a powder-like consistency.

The pulverization at step 1004 may, in at least some embodiments, yield pulverized cannabis with a particle size of 0.5 millimeter or less. This particle size may represent an average or maximum particle size of the cannabis after the pulverization. While the average particle size may be 0.5 millimeters or less, at least some of the particles may be greater than this threshold in at least some embodiments.

While not illustrated in FIG. 1, the pulverized *cannabis* may be filtered prior to step 1006 to ensure a desired and uniform particle size. For example, in some embodiments, the pulverized *cannabis* may be passed through one or more sieves. The sieves may be used to remove pulverized *cannabis* particles that are too big (or, in some embodiments too small). As noted above, the maximum size for the particles may be set to ensure sufficient surface area of the *cannabis*. In one embodiment, the sieve(s) may be configured such that the *cannabis* having a particle size of 0.5 mm or less is used in the subsequent steps of the method 1000.

In at least some embodiments, during operation 1006, the cannabis may be decarboxylated. More particularly, the cannabinoids in the cannabis may be decarboxylated. This process of decarboxylating the cannabinoids in the cannabis is referred to herein as decarboxylating the cannabis. Decarboxylation is the process of removing a carbon dioxide group from a molecule. Decarboxylation converts acidic cannabinoids, such as delta-9-tetrahydrocannabinolic acid (THCA) to neutral cannabinoids such as delta-9-tetrahydrocannabinol (THC).

The decarboxylation of the cannabis occurs by heating the cannabis. For example, in some embodiments, the decarboxylation is performed by heating the harvested & pulverized cannabis in an oven (e.g., by baking). The oven may be at a temperature of between 120 degrees Celsius and 140 degrees Celsius and the cannabis may be heated for a time period in the range of 30 minutes to 3 hours. It will be appreciated that the temperature of the oven and the bake time have an inverse relationship. For example, if the oven is at 120 degrees Celsius, then the bake time may be 60 minutes but if the oven is at 140 degrees Celsius, then the bake time may be only 30 minutes. The bake time is sufficiently long to permit decarboxylation, but short enough that the THC does not appreciably convert to cannabinol (CBN).

In an embodiment, the temperature of the oven is selected to be below the boiling point of the cannabinoids, flavonoids, and terpenoids found in cannabis. Flavonoids are a class of plant pigments. Terpenoids and Flavonoids are, in part, responsible for the look, taste and odor of a particular strain of cannabis. Terpenoids, which are structurally related to terpenes, are naturally occurring in a wide range of plants. In part, they contribute to what gives the plants their unique aromatic quality. Beta-sitosterol is a flavonoid which has a relatively low boiling point of 134 degrees Celsius (as compared with the boiling points of the other flavonoids, cannabinoids and terpenes commonly found in cannabis). Thus, in at least some embodiments, the decarboxylation is performed at a temperature that is less than the boiling point of 134 degrees Celsius. For example, in at least some embodiments, the temperature may be 130 degrees or less.

The oven used in the heating may be of the type described above with reference to step 1002. Other methods of heating the cannabis to decarboxylate the cannabis may be used in other embodiments (i.e. apart from the use of an oven).

Optionally, in some embodiments, operation 1006 of the method 1000 may be omitted so that the acidic form of the cannabinoids may be extracted from the cannabis rather than the neutral form of the cannabinoids. For example, the decarboxylation step 1006 may be performed where neutral cannabinoids, such as delta-9-tetrahydrocannabinol (THC), are desired, whereas the decarboxylation step 1006 may be omitted where acidic cannabinoids, such as delta-9-tetrahydrocannabinolic acid (THCA), are desired.

At step 1008 the pulverized cannabis (which has been decarboxylated if step 1006 is performed or not decarboxylated if step 1006 is not performed) is mixed with an extraction agent. In some embodiments, the extraction agent may be a medium chain triglycerides (MCT) powder. As an example, the MCT powder may have a fat content that is greater than 65%, a protein level that is greater than 25% and a carbohydrate level of less than one percent. The extraction agent and cannabis, when mixed may be referred to herein as a "premix" or "premixture" since the premix may be used in a subsequent mixture which will be described in greater detail below.

While the techniques described herein will function with MCT powder having various particle size profiles, the method 1000 has been tested and found to yield high extraction efficiencies using an MCT powder having a particle size which a minimum of 99% of particles fit pass through a US #10 sieve (i.e., 99% of particles are 2 mm or less).

The mixing at step 1008 uniformly mixes the cannabis with the MCT powder to produce a homogeneous and uniform mixture (i.e., the premix) without lumps. Uniform mixing may be achieved using a variable speed paddle mixer of the type commonly used in the baking and food industries. Mixing can be achieved, for example, at relatively low speeds for five to ten minutes or until a homogeneous mixture is produced having no lumps in order that all the pulverized cannabis is uniformly mixed with MCT powder and the maximum surface area of cannabis is exposed to facilitate extraction.

At step 1010, the premix produced at step 1008 may be sealed. The premix may be sealed in a manner that protects the premix from moisture and/or oxygen. For example, the premix may be sealed in a container (such as a heavy gauge plastic bag) which has been substantially vacated of oxygen. In at least some embodiments, the premix may be vacuum sealed. In other embodiments, the premix may be sealed using non-vacuum techniques which displace oxygen. For example, in some embodiments, nitrogen flushing may be used to displace oxygen in the container in which the premix is sealed.

The premix may then be stored (at step 1012) for a period of at least two days. This period may be referred to herein as an incubation period. During the incubation period, the mixture is placed in a cool and dark area. The method has been tested and found to yield high efficiency extraction when the mixture is placed in a room of approximately 18 degrees Celsius. However, the extraction will also occur at different temperatures, although there is likely a temperature to time relationship.

During the incubation period, cannabinoids are extracted from the cannabis and into the extraction agent. The amount of cannabinoids and other plant molecules that are extracted will depend on the incubation period. That is, longer incubation periods will generally result in greater extraction. A desired extraction level may, in some cases, be achieved in as little as two days while in other embodiments, longer extraction periods may be necessary or desirable. Other factors may also affect the incubation period required. For example, the strain of cannabis, particle size of the pulverized cannabis or MCT, storage conditions, etc. may affect the incubation period that is required to achieve a desired extraction level. Variables of the method may be altered or varied to maximize extraction of cannabinoids during the incubation period and/or to reduce the extraction time.

After the incubation period at step 1012 is complete, at step 1014 the premix produced at step 1008 may be exposed to water and the plant portion of the premix (i.e., the cannabis) may be filtered out. For example, the premix may be placed in a filtering apparatus and water may be added to the filtering apparatus to expose the premix to the water thereby creating a new mixture which includes the water and non-filtered components of the premix (e.g., the MCT and the cannabinoids and other plant molecules extracted from the cannabis). The new mixture is, therefore, a liquid mixture and may be referred to herein as a liquid mixture. In at least some embodiments, three ounces of water or more may be added per gram of the premix. The filtering may be performed in a relatively low pressure apparatus (e.g., 0 to 3 bar pressure) and the premix may be agitated during filtering to ensure uniform wetting of the premix and extraction of cannabinoids from the incubated premix. The plant material (i.e., the cannabis itself) is separated from the liquid mixture and the plant material may be discarded. Thus, the filtering may yield a mixture which includes water, dissolved MCT and cannabinoids extracted from the cannabis. A further filtering step may be used to clarify the liquid mixture. Other liquids and, in particular, relatively inert liquids may be used instead of or in addition to water provided such liquids do not otherwise affect the MCT-cannabinoid interaction. By way of further example, food-grade alcohol may be used instead of or in addition to water at operation 1014.

In some embodiments, instead of placing the premix in a filtering apparatus and adding water (or other liquids), the filtering in the presence of water may be performed by adding the premix to water (or other liquids), mixing, sonicating, or otherwise agitating the premix and the water (or other liquids) to dissolve the extraction agent (e.g., the MCT) in the water (or other liquids). In at least some embodiments, three ounces of water (or other liquids) or more may be added per gram of the premix. After the MCT is dissolved, the mixture may be filtered to remove the plant material (i.e., the cannabis itself) to yield a mixture which includes water (or other liquids), dissolved MCT and cannabinoids extracted from the cannabis. A further filtering step may be used to clarify the liquid mixture.

The water used at step 1014 may be hot or cold, although hot water may offer some benefits over cold water. For example, hot water may increase extraction efficiency and/or may provide decarboxylation. For example, in some embodiments in which the cannabis is not decarboxylated at operation 1006, the liquid mixture may be heated to decarboxylate the cannabinoids in the liquid mixture. While pre-decarboxylation (i.e., decarboxylating the plant at operation 1006 before creating the mixture) may be preferred in some embodiments, decarboxylation could instead be performed by heating the liquid mixture for an amount of time and at a temperature sufficient to decarboxlate the cannabinoids. Such temperatures and times are described above with respect to operation 1006 of the method 1000.

In other embodiments in which the cannabis is not decarboxylated at operation 1006, decarboxylation may not be performed by heating the liquid mixture. Instead, the cannabinoids may be left in their acidic form.

In some embodiments, the method 1000 may end at operation 1014. More specifically, after filtering of the plant material, the mixture obtained at operation 1014 may be considered to be the cannabis extract that is created using the method 1000 and this mixture may be used for direct consumption or another method may be employed to use the mixture in a food or beverage production process. For example, the mixture may be used to create a fresh beverage, added to a baked good, added to a beverage production process where the final beverage would be sterilized, etc. The liquid mixture obtained at operation 1014 is potable but may not be shelf stable and various techniques may be used to extend the shelf-life of the liquid mixture. To extend the shelf-life of the liquid mixture or beverages or food products created using the liquid mixture, the mixture or the products created using the mixture may be stored in a refrigerated environment.

In some embodiments, the liquid mixture obtained at step 1014 may be further processed to obtain a solid cannabis extract. For example, the liquid mixture may, at step 1016, be heated gently to evaporate the water. In at least some embodiments, the heating temperature may be below the denaturation temperature of the predominant proteins in the MCT. The heating continues until the water is evaporated away yielding solid particles, which will be referred to as cannabis extract. The cannabis extract may have less than one percent moisture content, in at least some embodiments. The cannabis extract obtained at operation 1016 is generally flake-like. This cannabis extract may be consumed using various techniques or may be processed into a consumable product such as a backed good, beverage, etc.

It has been found that the techniques for cannabinoid extraction described herein have a very high extraction efficiency. Indeed, tests indicate cannabinoid extraction efficiencies of greater than 70%.

While not illustrated in FIG. 1, in at least some embodiments, the *cannabis* extract produced according to the method 1000 may be further processed to, for example, reduce the particle size of the *cannabis* extract. For example, pulverization may be performed in the manner described above. The resulting powder can be added to food products, for example, to achieve a *cannabis*-infused edible with a specific concentration of THC, other cannabinoids and/or terpenes. The dry extracted powder homogenizes readily with both dry, oil-based and water based food and non-food systems.

In some embodiments, a tincture may be created by adding the cannabis extract to water and/or ethanol in sterile conditions in a good manufacturing practice (GMP) environment. The tincture can be added to water or other beverages or other liquids in order to deliver a certain quantity of THC, other cannabinoids and/or terpenes in a convenient and discreet manner. The tincture can also be used to add THC and cannabinoids to other food and non-food systems.

In using one version of the described method, non-decarboxylated cannabinoids, terpenoids and flavonoids could be extracted from pulverized cannabis as described by way of creating a pre-mix with MCT powder (as described at step 1008 of the method 1000) and incubating (as described at step 1012) for at least 2 days. This premix (which includes cannabis plant material which has not yet undergone decarboxylation) could then be dissolved and filtered to extract the non-decarboxylated cannabinoids, etc. so as to maximize the extraction of heat-labile components of the cannabis plant that might otherwise be lost or reduced through the heating process associated with decarboxylation. Once these medicinally active components have been extracted into the water phase as described (at operation 1014 of the method 1000), they can then be very carefully decarboxylated using much more uniform heating during the drying phase of the liquid. Since the medicinal components will be uniformly dispersed in the liquid phase, they can be heated more uniformly, maintaining a constant temperature of the liquid phase, in order to achieve decarboxylation of the cannabinoids with reduced loss of the volatile terpenoids and flavonoids. It can be noted that most other cannabinoid extraction processes tend to destroy the heat-labile medicinal components.

The various embodiments presented above are merely examples. Variations of the innovations described herein will be apparent to persons of ordinary skill in the art, such variations being within the intended scope of the present application. In particular, features from one or more of the above-described example embodiments may be selected to create alternative example embodiments including a sub-combination of features which may not be explicitly described above. In addition, features from one or more of the above-described example embodiments may be selected and combined to create alternative example embodiments including a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

What is claimed is:

1. A method of extracting cannabinoids from cannabis, the method comprising:
   preparing a premixture by mixing dried cannabis with an extraction agent, wherein the extraction agent is a medium chain triglycerides (MCT) powder;
   incubating the premixture; and
   after incubating the premixture, adding a liquid to the premixture to create a liquid mixture and filtering the cannabis from the mixture.

2. The method of claim 1, wherein the liquid is water.

3. The method of claim 1, further comprising, prior to mixing, pulverizing the cannabis to reduce a particle size of the cannabis.

4. The method of claim 1, wherein the MCT powder has a fat content that is greater than 65%, a protein level that is greater than 25% and a carbohydrate level of less than one percent.

5. The method of claim 1, further comprising:
   heating the liquid mixture to evaporate the liquid and produce a cannabis extract.

6. The method of claim 5, wherein the cannabis extract has a moisture content of one percent or less.

7. The method of claim 5, wherein heating the liquid mixture to evaporate the liquid comprises heating the liquid mixture at a temperature sufficient to decarboxylate.

8. The method of claim 1, wherein incubating comprises storing the premixture for between two and fifteen days.

9. The method of claim 1, further comprising, prior to incubating:
   vacuum sealing the premixture.

10. The method of claim 1, further comprising:
    after filtering the cannabis, further filtering the liquid mixture to clarify the liquid mixture.

11. The method of claim 1, further comprising, prior to preparing the premixture:
   decarboxylating the cannabis.

* * * * *